United States Patent
Daimon et al.

(10) Patent No.: US 7,655,923 B2
(45) Date of Patent: Feb. 2, 2010

(54) SPHERICAL ABERRATION CORRECTED ELECTROSTATIC LENS, INPUT LENS, ELECTRON SPECTROMETER, PHOTOEMISSION ELECTRON MICROSCOPE AND MEASURING SYSTEM

(75) Inventors: Hiroshi Daimon, Ikoma (JP); Hiroyuki Matsuda, Aioi (JP); Makoto Kato, Akishima (JP); Masato Kudo, Akishima (JP)

(73) Assignees: National University Corporation Nara Institute of Science and Technology, Nara (JP); Jeol, Ltd., Tokyo (JP)

( * ) Notice: Subject to any disclaimer, the term of this patent is extended or adjusted under 35 U.S.C. 154(b) by 191 days.

(21) Appl. No.: 11/631,296

(22) PCT Filed: Nov. 9, 2004

(86) PCT No.: PCT/JP2004/016602

§ 371 (c)(1),
(2), (4) Date: Jan. 3, 2008

(87) PCT Pub. No.: WO2006/008840

PCT Pub. Date: Jan. 26, 2006

(65) Prior Publication Data

US 2008/0135748 A1    Jun. 12, 2008

(30) Foreign Application Priority Data

Jul. 15, 2004    (JP) .............................. 2004-208926

(51) Int. Cl.
G21K 1/08     (2006.01)
H01J 3/14     (2006.01)
H01J 3/26     (2006.01)
H01J 49/42    (2006.01)

(52) U.S. Cl. .................. 250/396 R; 250/305; 250/311; 250/400; 850/9; 850/63; 378/43; 378/63; 378/161

(58) Field of Classification Search ................ 250/305, 250/311, 400, 396 R; 850/9, 63; 378/43, 378/63, 161
See application file for complete search history.

(56) References Cited

U.S. PATENT DOCUMENTS 4,358,680 A * 11/1982 Read ........................... 250/305

(Continued)

FOREIGN PATENT DOCUMENTS

EP    0 669 635    8/1995

(Continued)

OTHER PUBLICATIONS

"Approach for simultaneous measurement of two-dimensional angular distribution of charged particles: Spherical aberration correction using an ellipsoidal mesh", Matsuda, H,m Daimon, H, Kato, M. and Kudo, M., Physical Review E71, 066503, Jun. 2005.*

(Continued)

Primary Examiner—Bernard E Souw
Assistant Examiner—Meenakshi S Sahu
(74) Attorney, Agent, or Firm—Harness, Dickey & Pierce, P.L.C.

(57) ABSTRACT

A mesh (M) having an ellipsoid shape or a shape close to the ellipsoid shape is attached to an electrode (EL1) among electrodes (EL1 to ELn). Voltages of the later-stage electrodes (EL2 to ELn) are appropriately set. With this arrangement, a local negative spherical aberration generated by the mesh (M) is cancelled out with a positive spherical aberration. This optimizes an electric field distribution. As a result, this realizes an electrostatic lens whose acceptance angle is extended to about ±60°.

10 Claims, 6 Drawing Sheets

U.S. PATENT DOCUMENTS

| | | | |
|---|---|---|---|
| 4,764,673 A | * | 8/1988 | Bryson et al. ............... 250/305 |
| 5,315,113 A | | 5/1994 | Larson |
| 5,444,242 A | * | 8/1995 | Larson et al. ............... 250/305 |

FOREIGN PATENT DOCUMENTS

| | | | |
|---|---|---|---|
| JP | 56-107463 A | | 8/1981 |
| JP | 07-325052 | * | 12/1995 |
| JP | 7-325052 A | | 12/1995 |
| JP | 08-111199 | * | 4/1996 |
| JP | 8-111199 A | | 4/1996 |

OTHER PUBLICATIONS

"Electron optics development for photo-electron spectrometers", Wannberg, B., Nuclear Instruments and Methods in Physics Research A601, 2009, pp. 182-184.*

Search report by European Patent Office dated Sep. 21, 2009 for counterpart European application No. 04822204.

Kato M. et al "Spherical aberration correction of electrostatic lenses using spherical meshes" — Journal of Vacuum Science & Technology, Part A, Jul. 1995.

* cited by examiner

SPHERICAL ABERRATION CORRECTED ELECTROSTATIC LENS, INPUT LENS, ELECTRON SPECTROMETER, PHOTOEMISSION ELECTRON MICROSCOPE AND MEASURING SYSTEM

TECHNICAL FIELD

The present invention relates to a first-stage input lens for use in electron spectrometers such as XPS (X-ray Photoelectron Spectrometer), and AES (Auger Electron Spectrometer), and the like, and in PEEM (Photoemission Electron Emission Microscope).

BACKGROUND ART

In many conventional electron spectrometers, an electrostatic lens called as an input lens is used in an electron acceptance section of energy analyzer (typically, electrostatic semispherical analyzer). The input lens has functions of (i) accepting, as many as possible, electrons emitted from a specimen, (ii) decelerating the electron, and (iii) introducing the thus decelerated electron into the analyzer. In this way, the input lens improves energy resolution.

Moreover, some electron spectrometers are provided with a function of limiting a field of view through which the electron is accepted from a surface of the specimen. In the electron spectrometers having such an arrangement, their sensitivity is determined by how widely an angle is opened through which the electrons are accepted and introduced to the input lens. Moreover, an energy analyzer having a function of forming an image can, by forming the image from distribution of acceptance angles, measure angle dependency of an energy peak of photoelectrons at the same time when forming the image. In this case, as long as the acceptance angle is 90° or more, it is possible to measure at once angle dependencies for angles within a range of from an angle just off the surface to an perpendicular angle. Thus, this realizes efficient measurement of relationship between elements of a specimen and depth of the specimen.

However, a general electrostatic lens cannot focus, into one point, beams within a wide opening angle due to spherical aberration. Specifically, the acceptance angle for the general electrostatic lens is limited to be about ±20° or less.

Moreover, in a general photoemission electron microscope, a wide acceptance angle is realized by arranging such that photoelectrons and secondary electrons emitted from the specimens are accelerated and then introduced into an object lens. However, there are some cases that the acceptance angle becomes smaller because the electrons with large emission energy curve less. Specifically, when the emission energy is several hundred eV, the acceptance angle is about 30° (±15°) or less. If it becomes possible to perform measurement with a wide solid angle under the conditions that the emission energy is set at several hundred eV or more, this enables structural analysis of atomic arrangements, such as photoelectron diffraction and photoelectron holography. However, the acceptance angle of about 30° or less is insufficient for performing the structural analysis of atomic arrangements.

Furthermore, it has been proved that spherical aberration inevitably occurs in an electron lens, and that zero spherical aberration cannot be attained in a general lens configuration, in which a special electric charge in axial symmetry is not present. This prevents realization of a large acceptance angle. In view of this, there is an approach in which a mesh electrode or a foil electrode is provided on the way to the lens. This arrangement provides an effect equivalent to application of the special electric charge, thereby correcting the spherical aberration.

In case where the foil is used, it is necessary that the energy of the electrons be set high to some extent so that the electron beam can pass through the foil. It is possible to set the energy of the electors high in transmission electron microscopes or the like. However, it is difficult to set the energy of the electrons high in electron spectrometers which are used for measuring electrons having an energy of several keV at most.

Moreover, there is such a problem that it is difficult to shape the foil to have a curved surface, because, even if the electrons have a high energy, the foil should be sufficiently thin in order to prevent scattering of the electrons and the absorption of the electrons. Note that up to third order spherical aberration can be reduced to zero with a flat foil but it is difficult for the flat foil to cancel out higher order spherical aberration. In the electron microscope, high resolution is attained by narrowing the opening angle of the electron beams to an order of mrad. Thus, it is sufficient in the electron microscope that at least the third order spherical aberration can be corrected. However, the foil is not an effective means for correcting the spherical aberration for the beams within an opening angle of several tens degrees, which is required in electron spectrometers.

The aforementioned problems associated with the correction using the foil can be solved by using a mesh in lieu of the foil. The use of the mesh solves the problem in the transmission property. Further, compared with the foil, it is easier to shape the mesh to give it a curved surface. Conventionally, as described in Japanese Patent Application, Tokukaihei, Publication No. 8-111199 (published on Apr. 30, 1996), use of a spherical mesh is proposed to improve the aberration (see FIG. 8). The use of the spherical mesh attains an acceptance angle as high as ±30°.

DISCLOSURE OF INVENTION

An object of the present invention is to attain a wider acceptance angle than in use of a spherical mesh.

In order to attain the object, a spherical aberration corrected electrostatic lens is provided with: a single mesh located so as to form a magnified virtual image having a negative spherical aberration, for electrons or ions emitted within a certain opening angle from a predetermined position of an object plane, the mesh having an ellipsoid shape or a shape close to the ellipsoid shape, and being concave toward the object plane and axially symmetric about an optical axis; and a plurality of electrodes, located concentrically with an optical axis and in a position between the mesh and an image plane, for generating a convergent electric field that forms a real image from the magnified virtual image and generates a positive spherical aberration, the plurality of electrodes having concentric surfaces.

In order to attain higher focusing property, it is preferable to correct a blur of the real image by finely adjusting the shape of the mesh in the electrostatic lens provided with: the single mesh located so as to form the magnified virtual image having the negative spherical aberration, for the electrons or ions emitted within the certain opening angle from the predetermined position of the object plane, the mesh having the ellipsoid shape or the shape close to the ellipsoid shape, and being concave toward the object plane and axially symmetric about the optical axis; and the plurality of electrodes, located concentrically with an optical axis and in the position between the mesh and the image plane, for generating the convergent electric field that forms the real image from the magnified virtual image and generates the positive spherical aberration, the plurality of electrodes having the concentric surfaces.

According to the spherical aberration corrected electrostatic lens of the present invention, the spherical aberration is corrected by using non-spherical mesh. In this way, an acceptance angle of ±60° is realized. Sensitivity of a lens is proportional to square of the acceptance angle. Therefore, dramatic improvement in sensitivity and performance is expected in using this lens as a first stage of an input lens of an electron spectrometer system.

For a fuller understanding of the nature and advantages of the invention, reference should be made to the ensuing detailed description taken in conjunction with the accompanying drawings.

BEST MODE FOR CARRYING OUT THE INVENTION

1. Spherical Aberration Corrected Electrostatic Lens According to the Present Invention In FIG. 1, an embodiment of the spherical aberration corrected electrostatic lens according to the present invention is illustrated. The lens is provided with a mesh M, a plurality of electrodes EL1 to ELn, and a power source (not shown). The mesh M has an ellipsoid shape or a shape close to the ellipsoid shape, and is axially symmetric about an optical axis. The mesh M, which is concave toward an object plane, is so as to form a magnified virtual image having a negative spherical aberration, for electron beams or ion beams emitted within a certain opening angle from a predetermined position of the object plane. The plurality of electrodes EL1 to ELn, which have concentric surfaces, form a convergent electric field that form a real image from the magnified virtual image and generate a positive spherical aberration. The power source is used for respectively applying arbitrary voltages onto the electrodes. Here, the mesh M is connected to the first electrode EL1 and given with the same potential as the first electrode EL1.

Figure 2:
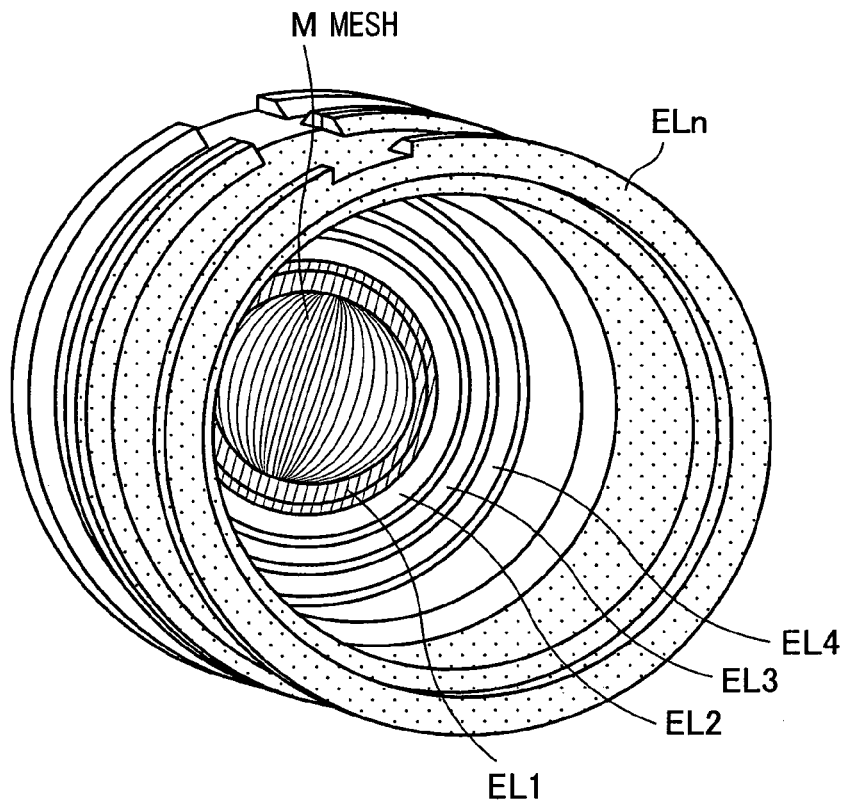
FIGS. 2(a) and 2(b) are perspective views illustrating the spherical aberration corrected electrostatic lens according to the embodiment of the present invention.
Figure 2:
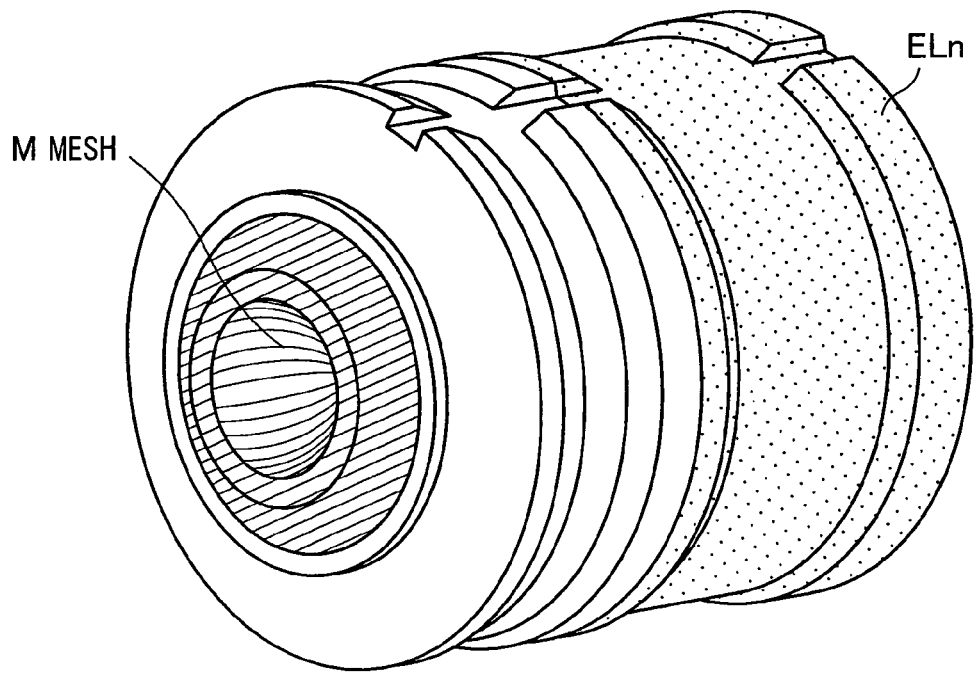

FIGS. 2(a) and 2(b) are perspective views of the spherical aberration corrected electrostatic lens according to the embodiment of the present invention. Note that FIG. 2(a) is the perspective view in which the spherical aberration corrected electrostatic lens according to the embodiment of the present invention is viewed from a direction toward which the mesh is protruded, whereas FIG. 2(b) is the perspective view in which the spherical aberration corrected electrostatic lens according to the embodiment of the present invention is viewed from a direction opposite to the direction toward which the mesh is protruded.

Figure 1:
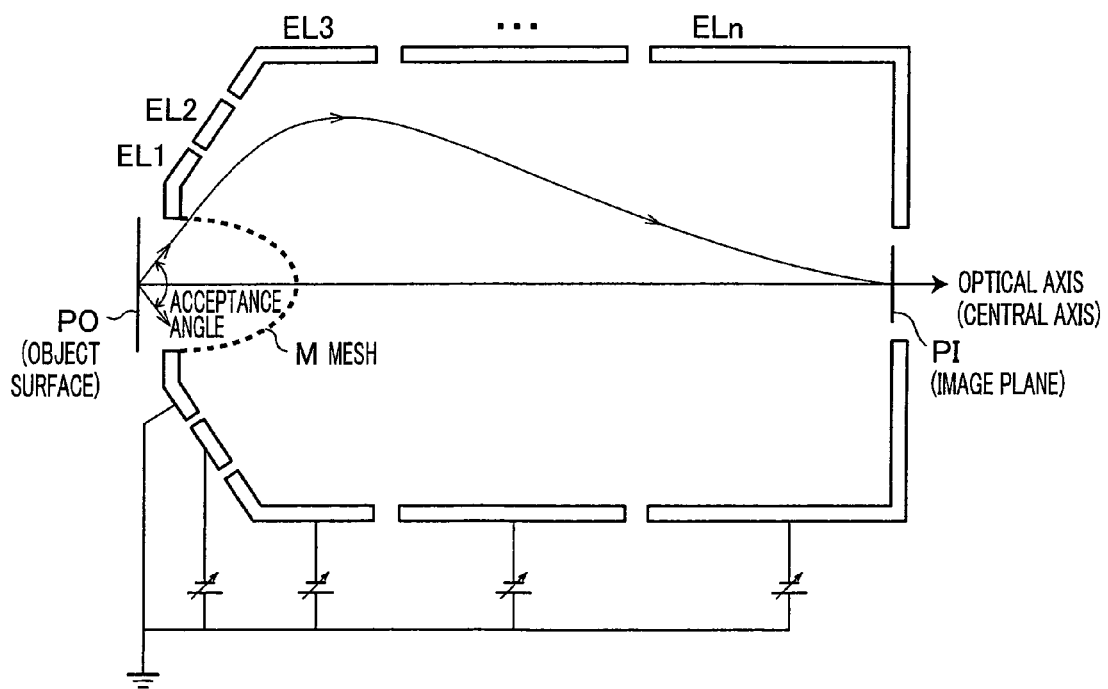
FIG. 1 is a view illustrating an embodiment of a spherical aberration corrected electrostatic lens according to the present invention.

As illustrated in FIGS. 1, 2(a), and 2(b), the spherical aberration corrected electrostatic lens is provided with the mesh M, and the electrodes EL1 to ELn. The electrodes EL1 to ELn are shaped in concentric circles. Note that the mesh M and the electrode EL1 are hatched in the same manner in FIGS. 2(a) and 2(b). This indicates that they have the same potential.

A magnetic field lens may be used as the electrodes EL2 to ELn shaped in the concentric circles. The use of the magnetic field lens is advantageous because electric discharge from the electrodes can be prevented by the use of the magnetic field lens.

A principle behind the correction of the spherical aberration by the lens illustrated in FIG. 1 is as follows: the negative spherical aberration is locally generated by an electric field formed around the mesh M. Then, the negative spherical aberration is cancelled out with the positive spherical aberration generated by the convergent electric field. In this way, a magnified image whose blur is corrected is formed on an image plane PI.

Note that, as described above, it becomes difficult for the spherical mesh to perform the correction if the acceptance angle becomes about ±30° or more. In view of this, the present invention is so arranged that the mesh having the ellipsoid shape or a shape close to the ellipsoid shape is used. With this arrangement, a very large acceptance angle is realized in the present invention. Moreover, for the beams of an emission angle of up to ±30°, the use of the spherical mesh can give an electric field that is relatively substantially ideal. However, if used for the beam of an emission angle of about ±30° or more, the electric field given by the use of such mesh would be remarkably far from the ideal, and thus cause significant effect toward the central axis. This would result in a large spherical aberration.

This problem can be solved by arranging such that the electric field is so shaped that a force toward the central axis changes effectively largely with respect to a beam having a relatively small emission angle. In order to shape the electric field as such, the shape of the mesh should be an ellipsoid shape whose major axis is along an optical axis direction or a shape close to the ellipsoid shape, rather than the spherical shape.

The reason why it is arranged such that the mesh is ellipsoid but not spherical is as follows: premise for the large acceptance angle is that the mesh has a large opening angle as a whole with respect to an electron beam source for the object plane, regardless of the shape of the mesh. If the mesh is spherical, the electron beam source need be located closer to the mesh up to a vicinity of its center of curvature, for attaining the large opening angle of the mesh. However, this indicates that the orbital of the electrons passing through the mesh and the surface of the mesh cross each other at an angle close to the right angle.

Because of this, refracting effect given to the electrons passing through the mesh becomes almost negligible. Thus, it becomes difficult for the lens to obtain the focusing effect, which the lens should have. Therefore, in order to increase the refracting effect given to the electrons passing through the mesh, it is arranged such that the mesh has the ellipsoid surface whose major axis is along the optical axis direction. Such an ellipsoid surface has a larger curvature with respect to the central axis.

Moreover, in the spherical aberration corrected electrostatic lens shown in FIG. 1, the shapes and locations of the mesh M and the electrodes EL1 to ELn, and voltages to applied thereon are so designed that the negative spherical aberration generated near the mesh will be cancelled out with the positive spherical aberration generated by the convergent electric field. Moreover, the number of the electrodes may be changed so as to be appropriate for design.

Figure 3:
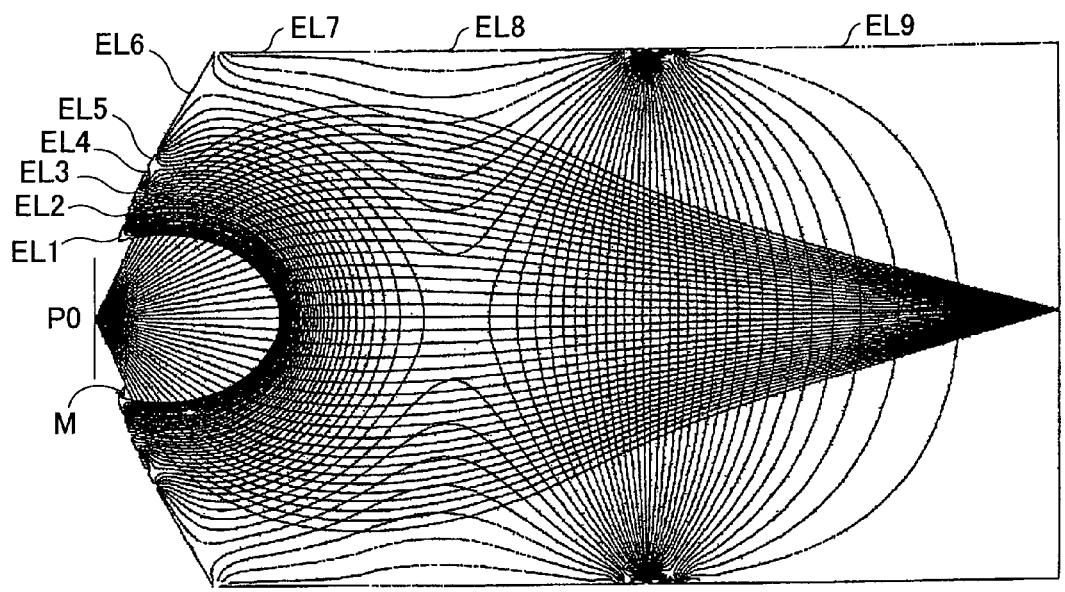
FIG. 3 is a diagram depicting a result of calculation of electron trajectories in the lens according to the embodiment of the present invention.

FIG. 3 is a diagram illustrating results of calculation of the electron trajectories with respect to the lens according to the embodiment of the present invention. Note that the lens in FIG. 3 is provided with the mesh M and multi-segmented electrodes EL1 to EL9 arranged from the vicinity of the mesh M. Moreover, the first electrode EL1 and the electrode EL9 that is located farthest from the mesh are given an earth potential. With this lens, an acceptance angle of ±60° is realized. Note that the number of the electrodes may be eight or less, or ten or more, even though the lens illustrated in FIG. 3 is provided with nine electrodes. Moreover, the first electrode EL1 and the electrode EL9 that is located farthest from the mesh are given a potential other than the earth potential. Especially, with an arrangement in which the potential of the first electrode EL1 is positive, it becomes possible to adopt a small mesh to receive the electrons within a wide range.

The spherical aberration cannot be completely solved with the mesh having an exact ellipsoid surface. When a distance between the object plane to the image surface is 500 mm, a blur of about 1 mm occurs at a focusing point. The blur suppressed to about 1 mm is sufficient for the general electron spectrometer in which a slit having a several mm width is provided at an inlet of the analyzer.

Meanwhile, if zero spherical aberration is strictly required, the ellipsoid shape of the mesh is finely adjusted. In this case, it is necessary that the shape of the mesh be expressed in polynomial expansion or in a numerical value. In FIG. 3, the electron trajectories obtained after the fine adjustment is shown.

Specifically, the shape of the mesh used in the spherical aberration corrected electrostatic lens illustrated in FIG. 3 is approximately expressed by the following equation (see FIG. 4):

$$\frac{(z-z0)^2}{A^2} + \frac{r^2}{B^2} = 1$$

Here, the ellipsoid had a long radius A of 83.928 mm and a short radius diameter B of 50.826 mm. A distance z0 between an original point O on the object plane to a center OOV of the ellipsoid was 49.828 mm. Moreover, a distance z1 from the object plane to the mesh was 17.416 mm.

The fine adjustment of the mesh shape was carried out by using the following equation that defines a displacement $\Delta R(\theta)$ after the fine adjustment of the ellipsoid shape of the mesh, in order to find out optimized parameters a0, a1 to an, which could minimize the spherical aberration.

$$\Delta R(\theta) = a0 + a1\cos(\theta) + a2\cos(2\theta) + a3\cos(3\theta) + \ldots + an\cos(n\theta)$$

Note that the displacement $\Delta R(\theta)$ is an amount of change in a distance R with respect to the mesh shape after the fine adjustment, where (R, θ) is spherical coordinates whose center is at the original point O on the object plane. The distance R is a distance between the original point O to the ellipsoid. The parameter values obtained as a result of the optimization are listed in Table 1.

TABLE 1

| i | a(i) | a(i + 1) | a(i + 2) | a(i + 3) |
|---|---|---|---|---|
| 0 | 0.02276534 | −0.04595226 | 0.2025693 | −1.01626032 |
| 4 | 0.80852427 | 3.43616484 | −5.28589311 | −1.91051272 |
| 8 | 3.8492545 | 6.54714045 | 8.17070334 | −60.87155409 |
| 12 | 66.27121148 | 31.04915991 | −104.2805696 | 17.41064024 |
| 16 | 130.9126232 | −179.4638207 | 181.1198638 | −219.8278809 |
| 20 | 184.204988 | −46.61989035 | 28.21433024 | −158.9245447 |
| 24 | 125.782988 | 149.3363534 | −309.5966193 | 128.8125736 |
| 28 | 251.0895235 | −621.7407591 | 761.1740088 | −477.7010587 |
| 32 | −14.2581134 | 283.8178842 | −374.1945141 | 546.4842967 |
| 36 | −568.380405 | 236.5440682 | −40.56115109 | 273.5107002 |
| 40 | −365.569348 | −2.81491568 | 284.9194824 | −166.3241255 |
| 44 | −18.0626652 | 130.9309417 | −239.0143786 | 133.8375943 |
| 48 | 119.7297615 | −47.00716256 | −195.544336 | 8.46264561 |
| 52 | 310.3231261 | −115.921384 | −138.3852572 | −148.9387069 |
| 56 | 327.161727 | 131.1421784 | −300.1810874 | −435.2307328 |
| 60 | 958.9327807 | −301.5418878 | −684.3534237 | 794.0595384 |
| 64 | −234.004749 | −79.61908303 | −41.92264024 | 135.8530778 |
| 68 | −17.4977807 | −51.69557301 | −37.97415163 | 60.69282065 |
| 72 | 54.37255907 | −101.458482 | 66.58466784 | −94.83679587 |
| 76 | 24.97081501 | 292.2071153 | −449.4793955 | 107.3526022 |
| 80 | 285.0491811 | −234.6846462 | 21.64295228 | −32.09396229 |
| 84 | 73.60854535 | 53.88984232 | −125.9065371 | 14.58811256 |
| 88 | 82.90382007 | −70.29707719 | 37.43264945 | −4.49405482 |
| 92 | −32.3934338 | 16.71906933 | 20.93529348 | 2.05117546 |
| 96 | −36.6298845 | 8.90061712 | 18.17126481 | 13.7116175 |
| 100 | −43.6836161 | 28.14901298 | −4.11948962 | −5.92126201 |
| 104 | 9.03492074 | −2.82089267 | −2.98328988 | −4.73646922 |
| 108 | 7.98990766 | 2.37061122 | −3.58382089 | −4.00691688 |
| 112 | −1.11020061 | 6.00546624 | 8.39009059 | −20.90705838 |
| 116 | 14.1196407 | −4.98924185 | 2.44765695 | 1.49563757 |
| 120 | −2.73082197 | −2.80914392 | 8.09108793 | −17.04443968 |
| 124 | 31.70669925 | −29.21133675 | 1.88340672 | 17.41459377 |
| 128 | −10.5427924 | 0.41411998 | −0.30705446 | −2.11773674 |
| 132 | 7.21992635 | −5.06957235 | 1.66541034 | −4.06774591 |
| 136 | 4.81034286 | −1.77991805 | 2.23786435 | −3.54505788 |
| 140 | −0.22944973 | 2.76150478 | 0.39577453 | −1.46766283 |
| 144 | −1.88724356 | 1.81152873 | 1.9363094 | −1.95014515 |
| 148 | −1.12615135 | 1.41842975 | 0.24026101 | −0.24927497 |
| 152 | −0.34733963 | −0.04154328 | 0.18479182 | 0.28302996 |
| 156 | −0.27339714 | 0.04216784 | −0.24859575 | 0.3015522 |
| 160 | 0.05309796 | −0.1100368 | −0.14537415 | 0.11823244 |
| 164 | 0.05109639 | 0.04352473 | −0.17216657 | 0.0919959 |
| 168 | −0.0439265 | 0.13863717 | −0.15263893 | 0.0468879 |
| 172 | −0.00586276 | 0.04421637 | −0.03210722 | −0.03473107 |
| 176 | 0.06525243 | −0.04219697 | 0.0130231 | −0.0015416 |

Moreover, carried out was simulation to find out how to set an ellipticity (A/B in Equation 1) of the mesh in order to realize a preferable acceptance angle, for example, ±60°. Results of the simulation are as follows.

Figure 4:
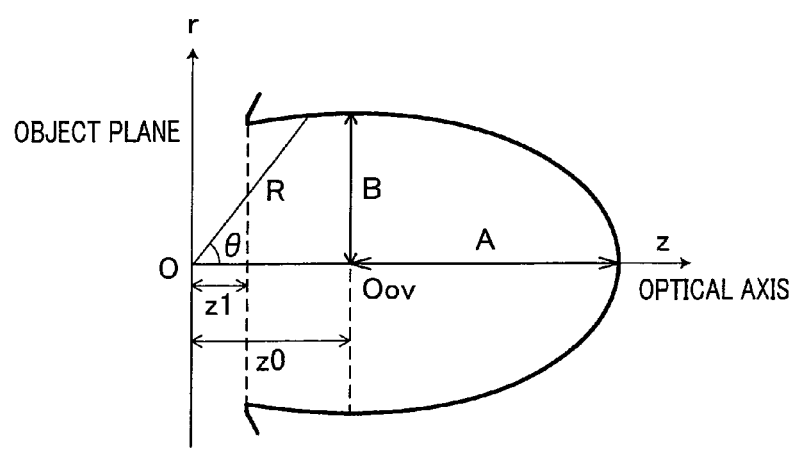
FIG. 4 is a diagram for explaining an approximate expression of a shape of a mesh provided to the lens depicted in FIG. 3.

In reality, besides the ellipticity, locations of the center of the ellipsoid and an aperture of the mesh, that is z0 and z1, are important in the optimization of the shape of the mesh (see FIG. 4). However, in the results shown below, the locations of the center of the ellipsoid and the aperture of the mesh were fixed as z0=46.933 mm and z1=21.333 mm, in order to observe only an effect caused by the change in the ellipticity.

Figure 5:
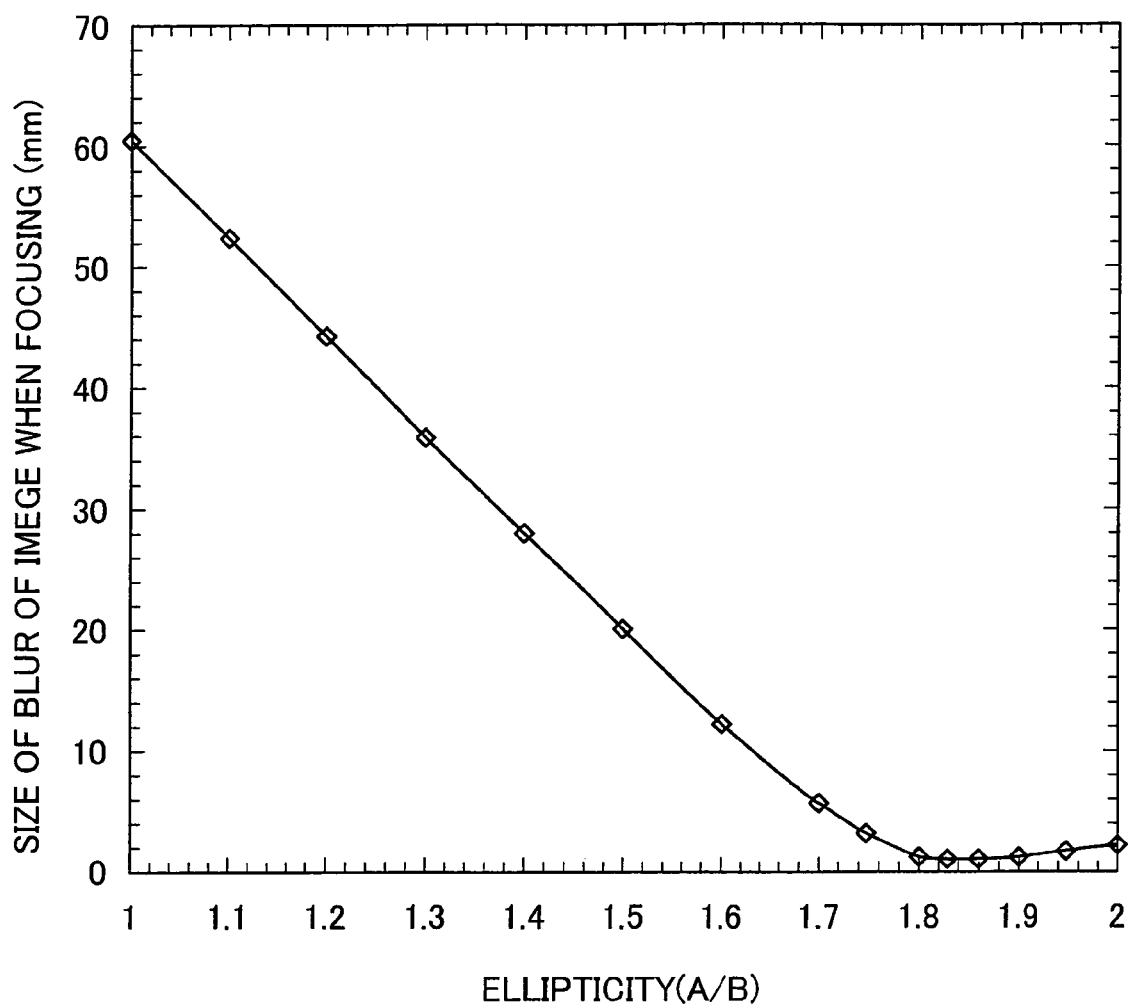
FIG. 5 is a graph depicting how (a) a size of blur of an image when focusing and (b) an ellipticity of the mesh are related with each other in the spherical aberration corrected electrostatic lens according to the present invention.

FIG. 5 is a graph depicting how (a) a size of blur of an image when focusing and (b) an ellipticity of the mesh are related with each other in the spherical aberration corrected electrostatic lens according to the present invention. Note that the acceptance angle of the spherical aberration corrected electrostatic lens was set to 60° in the simulation of the size of the blur in focusing depicted in FIG. 5.

As illustrated in FIG. 5, as the value A/B was increased from 1, the size of the blur in focusing was reduced. At the ellipticity of about 1.8, the size of the blur in focusing reached approximately zero.

At A/B=1, that is, the shape of the mesh was spherical, the spherical aberration was not corrected. As the A/B became larger so as to cause the shape of the mesh to be more ellipsoidal, the spherical aberration could be corrected more efficiently. Thus, when the acceptance angle of the spherical aberration corrected electrostatic lens is set to 60°, most efficient correction can be attained at A/B of about 1.8.

2. Devices in which Spherical Aberration Corrected Electrostatic Lens According to Present Invention is Applicable The spherical aberration corrected electrostatic lens according to the present invention is applicable in various charged particle optical devices, for example, electron spectrometers, photoemission electron microscopes. In the following, arrangements of an electron spectrometer and a photoemission electron microscope in which the spherical aberration corrected electrostatic lens according to the present invention is adopted.

Figure 6:
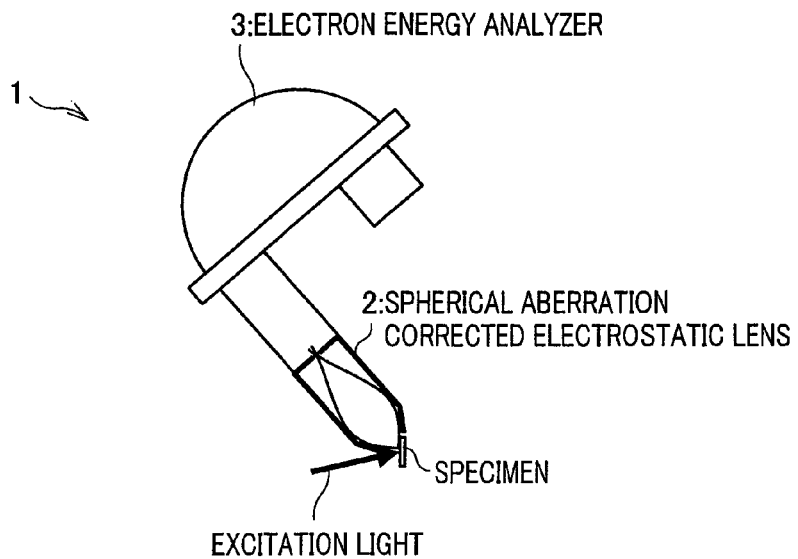
FIG. 6 is a diagram illustrating an example of an arrangement of an electron spectrometer in which the spherical aberration corrected electrostatic lens according to the present invention is adopted.

FIG. 6 is a diagram illustrating an example of an arrangement of an electron spectrometer in which the spherical aberration corrected electrostatic lens according to the present invention is adopted. As shown in FIG. 6, an electron spectrometer 1 is provided with a spherical aberration corrected electrostatic lens 2 according to the present invention, and an electron energy analyzer 3.

Because it is provided with the spherical aberration corrected electrostatic lens 2 according to the present invention, the electron spectrometer 1 having the above arrangement can detect photoelectrons from a specimen with high sensitivity. Thus, use of the electron spectrometer 1 allows detailed analysis of the specimen.

Figure 7:
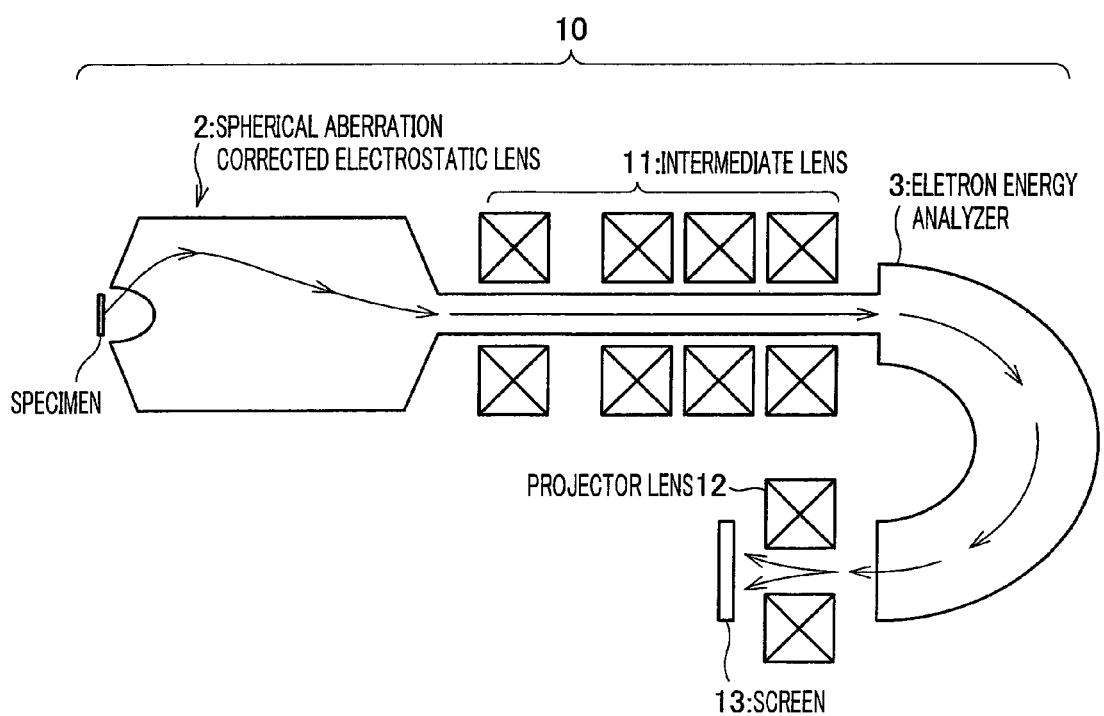
FIG. 7 is a diagram illustrating an example of a photoemission electron microscope in which the spherical aberration corrected electrostatic lens according to the present invention is adopted.
Figure 8:
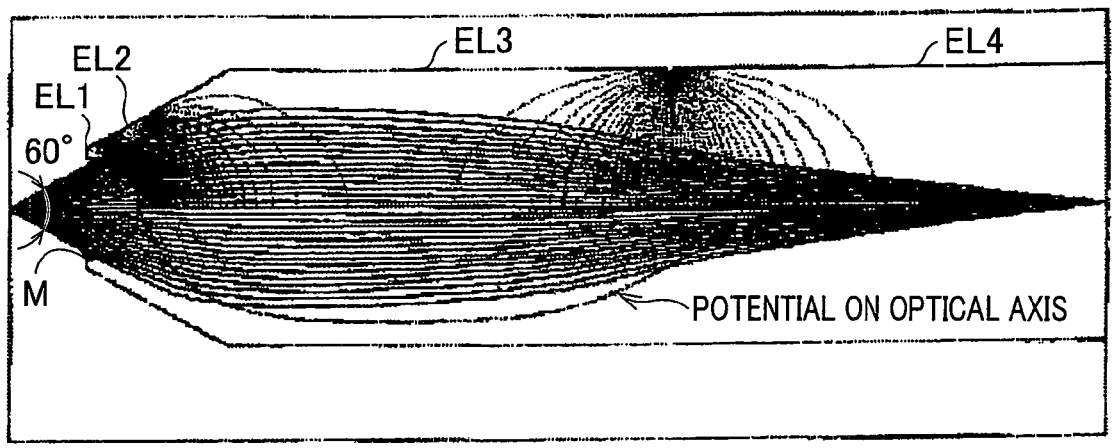
FIG. 8 is a cross sectional view of a conventional spherical aberration corrected electrostatic lens having a spherical mesh.

FIG. 7 is a diagram illustrating an example of a photoemission electron microscope in which the spherical aberration corrected electrostatic lens according to the present invention is adopted. As shown in FIG. 7, a photoemission electron microscope 10 is provided with a spherical aberration corrected electrostatic lens 2 according to the present invention, an intermediate lens 11, an electron energy analyzer 3, a projector lens 12 and a screen 13.

Because it is provided with the spherical aberration corrected electrostatic lens 2 according to the present invention, the photoemission electron microscope 10 having the above arrangement can detect photoelectrons from a specimen with high sensitivity. Thus, use of the photoelectron microscope 10 allows detailed analysis of the specimen.

Note that the spherical aberration corrected electrostatic lens according to the present invention is applicable to a measuring system including (a) the photoelectron spectrometer provided with the same lens, or (b) a spherical aberration corrected electrostatic lens. Because the spherical aberration corrected electrostatic lens according to the present invention is provided, such measuring system allows detailed analysis of a measurement object.

The invention being thus described, it will be obvious that the same way may be varied in many ways. Such variations are not to be regarded as a departure from the spirit and scope of the invention, and all such modifications as would be obvious to one skilled in the art are intended to be included within the scope of the following claims.

INDUSTRIAL APPLICABILITY

According to a spherical aberration corrected electrostatic lens of the present invention, it is possible to have a wider acceptance angle than in the use of the spherical mesh. Thus, dramatic improvement in sensitivity and performance is expected in using the spherical aberration corrected electrostatic lens according to the present invention as a first stage of an input lens of an electron spectrometer system such as electron spectrometers, photoemission electron microscopes, and the like. Further, by arranging such that the input lens is provided with a mesh for accelerating or decelerating electrons or ions, it is possible to arbitrarily set energy of photoelectrons having passed through the mesh. This does not only attain easy focusing but also allows measurement of photoelectrons having low energy.

The invention claimed is:

1. A spherical aberration corrected electrostatic lens, comprising:
   a mesh located so as to form a magnified virtual image having a negative spherical aberration, for electrons or an ion beam emitted within a certain opening angle from a predetermined position of an object plane, the mesh having an ellipsoid shape, the ellipsoid including a short radius and a long radius such that a ratio of the long radius to the short radius is in a range of 1.5 to 2, and being concave toward the object plane and symmetrical along an optical axis; and
   a plurality of electrodes, located concentrically with an optical axis and in a position between the mesh and an image plane, for generating a convergent electric field that forms a real image from the magnified virtual image and generates a positive spherical aberration, the plurality of electrodes having concentric surfaces.

2. A spherical aberration corrected electrostatic lens, comprising:
   a mesh located so as to form a magnified virtual image having a negative spherical aberration, from electrons or an ion beam emitted within a certain opening angle from a predetermined position of an object plane, the mesh having a shape prepared by fine adjustment of an ellipsoid shape, the fine adjustment being performed by $\Delta R$, $\Delta R$ being a displacement expressed as a sum of a function of at least three terms and including a variable of $\theta$, wherein a spherical coordinate whose center is at an origin point is expressed as $(R, \theta)$, $R$ being a distance between an origin point on an object plane and a point on the ellipsoid, and $\theta$ being an angle between (a) a line connecting the origin point on the object plane and the point on the ellipsoid and (b) a long axis of the ellipsoid, and being concave toward the object plane and symmetrical along an optical axis; and
   a plurality of electrodes, located concentrically with an optical axis and in a position between the mesh and an image plane, for generating a convergent electric field that forms a real image from the magnified virtual image and generates a positive spherical aberration, the plurality of electrodes having concentric surfaces.

3. The spherical aberration corrected electrostatic lens as set forth in claim 1, wherein:
   the ratio of the long radius to the short radius is in a range of 1.7 to 2 when the ion beam is accepted at an angle of approximately ±60°.

4. The spherical aberration corrected electrostatic lens as set forth in claim 1, wherein:
the shape of the ellipsoid is expressed by the following equation:

$$\frac{(z-z0)^2}{A^2} + \frac{r^2}{B^2} = 1$$

where z is a distance, along an optical axis, between an original point on an object plane and a point on the ellipsoid, z0 is a distance between the original point on the object plane to a center of the ellipsoid, A is a long radius of the ellipsoid, B is a short radius of the ellipsoid, and r is a distance, in a direction vertical to the optical axis, between the optical axis and the point on the ellipsoid.

5. The spherical aberration corrected electrostatic lens as set forth in claim 2, wherein:
the shape prepared by the fine adjustment of the ellipsoid shape has a short radius and a long radius in such a manner that a ratio of the long radius to the short radius is in a range of 1.5 to 2.

6. The spherical aberration corrected electrostatic lens as set forth in claim 5, wherein:
the ratio of the long radius to the short radius is in a range of 1.7 to 2 when the ion beam is accepted at an angle of approximately ±60°.

7. An input lens, comprising:
a spherical aberration corrected electrostatic lens, comprising:
a mesh, located so as to form a magnified virtual image having a negative spherical aberration, for electrons or an ion beam emitted within a certain opening angle from a predetermined position of an object plane, the mesh having an ellipsoid shape, the ellipsoid having a short radius and a long radius in such a manner that a ratio of the long radius to the short radius is in a range of 1.5 to 2, and being concave toward the object plane and symmetrical along an optical axis; and
a plurality of electrodes, located concentrically with an optical axis and in a position between the mesh and an image plane, for generating a convergent electric field that forms a real image from the magnified virtual image and generates a positive spherical aberration, the plurality of electrodes having concentric surfaces, and
at least one mesh, between the predetermined object plane and the spherical aberration corrected electrostatic lens, for accelerating or decelerating the electrons or ions.

8. An electron spectrometer, comprising:
a spherical aberration corrected electrostatic lens, comprising:
a mesh, located so as to form a magnified virtual image having a negative spherical aberration, for electrons or an ion beam emitted within a certain opening angle from a predetermined position of an object plane, the mesh having an ellipsoid shape, the ellipsoid having a short radius and a long radius in such a manner that a ratio of the long radius to the short radius is in a range of 1.5 to 2, and being concave toward the object plane and symmetrical along an optical axis; and
a plurality of electrodes, located concentrically with an optical axis and in a position between the mesh and an image plane, for generating a convergent electric field that forms a real image from the magnified virtual image and generates a positive spherical aberration, the plurality of electrodes having concentric surfaces.

9. A photoemission electron microscope, comprising:
a spherical aberration corrected electrostatic lens, comprising:
a mesh, located so as to form a magnified virtual image having a negative spherical aberration, for electrons or an ion beam emitted within a certain opening angle from a predetermined position of an object plane, the mesh having an ellipsoid shape, the ellipsoid having a short radius and a long radius in such a manner that a ratio of the long radius to the short radius is in a range of 1.5 to 2, and being concave toward the object plane and symmetrical along an optical axis; and
a plurality of electrodes, located concentrically with an optical axis and in a position between the mesh and an image plane, for generating a convergent electric field that forms a real image from the magnified virtual image and generates a positive spherical aberration, the plurality of electrodes having concentric surfaces.

10. A measuring system, comprising:
at least one of an electron spectrometer; and
a photoemission electron microscope, the electron spectrometer and the photoemission electron microscope each comprising:
a spherical aberration corrected electrostatic lens, comprising:
a mesh, located so as to form a magnified virtual image having a negative spherical aberration, for electrons or an ion beam emitted within a certain opening angle from a predetermined position of an object plane, the mesh having an ellipsoid shape, the ellipsoid having a short radius and a long radius in such a manner that a ratio of the long radius to the short radius is in a range of 1.5 to 2, and being concave toward the object plane and symmetrical along an optical axis, and
a plurality of electrodes, located concentrically with an optical axis and in a position between the mesh and an image plane, for generating a convergent electric field that forms a real image from the magnified virtual image and generates a positive spherical aberration, the plurality of electrodes having concentric surfaces.

* * * * *